United States Patent [19]

Young

[11] 4,104,126

[45] Aug. 1, 1978

[54] NON-ISOTOPIC SUBSTRATE ASSAY EMPLOYING BACTERIOLYSIS PRODUCTS

[75] Inventor: David M. Young, Sherborn, Mass.

[73] Assignee: Nichols Institute of Endocrinology, Inc., San Pedro, Calif.

[21] Appl. No.: 743,413

[22] Filed: Nov. 19, 1976

Related U.S. Application Data

[63] Continuation of Ser. No. 653,455, Jan. 29, 1976, abandoned.

[51] Int. Cl.² ............................................. G01N 31/14
[52] U.S. Cl. ..................... 195/103.5 A; 195/103.5 V; 195/103.5 R
[58] Field of Search ................. 195/103.5 R, 103.5 A, 195/103.5 V

[56] References Cited

U.S. PATENT DOCUMENTS 3,910,824  10/1975  Cartwright et al. ........... 195/103.5 A

OTHER PUBLICATIONS

Science, vol. 164, pp. 1279 & 1280 (1969).

*Primary Examiner*—Alvin E. Tanenholtz
*Attorney, Agent, or Firm*—Lyon & Lyon

[57] ABSTRACT

Substrates such as haptens and antigens, and those for receptor proteins and native circulating binding proteins are assayed by determining bacteriolysis products occasioned by bacteriophage infection of host cells, in a modification of the "chemically modified bacteriophage assay." Thus, a substrate such as an antigen is conjugated with bacteriophage and the conjugate competes with antigen in the specimen under assay for a limited number of binding sites on antibody. Phage conjugate surviving antibody inactivation is quantified by determining intracellular constituents of host bacteria subsequently infected by the bacteriophage remaining viable, which latter can be related to the levels of antigen originally present in the specimen. A preferred embodiment involves colorimetric assay for beta galactosidase freed by phage lysis of *E. coli*. Generally, the method is of sensitivity comparable to that of radioimmunoassay, but is attended by substantial advantages not common to the latter technique. The method is far less cumbersome than the plaque-containing techniques hitherto employed in bacteriophage assays.

16 Claims, No Drawings

NON-ISOTOPIC SUBSTRATE ASSAY EMPLOYING BACTERIOLYSIS PRODUCTS

This is a continuation, of application Ser. No. 653,455 filed Jan. 29, 1976 and now abandoned.

BACKGROUND AND SUMMARY OF THE INVENTION

In recent years the diagnostic arts have come increasingly to employ and rely upon the detection of minute quantities of physiologically important substances innately or adventitiously present in the body. Many such assays involve competition for a limited number of binding sites on specific binding proteins such as antibodies. These techniques have proven both more sensitive and less cumbersome than earlier resorts such as colorimetry and fluorometry. For example, in the last decade or so radioimmunoassay has proven a tool of exquisite sensitivity and specificity in assays for hormones and other substances, permitting their detection in levels ranging down to fractions of a nanogram per milliliter. Commonly, radioimmunoassay involves competition of radioactively labeled antigen and native antigen for antibody, whereafter bound or unbound label is counted and native antigen substractively quantitated. In like manner, other specific binding proteins such as thyroid binding globulin and estradiol receptor protein have been employed in radiometric determinations of their substrates. Despite the capabilities which commend them, radioimmunoassay and related radiometric determinations of physiologically important substances leave much to be desired on several fronts. For example, counting equipment is expensive, isotopes may be hazardous to health and are in any event plagued by undesirably short half-lives, free and bound substrate must be separated before counting, the radioactively labeled antigen in some cases differs in specificity from the untagged target of the assay, and the technique is not as amenable to full automation as might be desired. In some quarters, recognition of these disabilities has focused attention on the so-called "chemically modified bacteriophage assay" first reported by Makela, *Immunology*, 10, 81 (1966) and independently by Haimovich and Sela, *J. Immunology*, 97, 338 (1966).

A bacteriophage is a bacteriolytic nucleoprotein which, like any virus, injects its genetic content into its host (in the case of bacteriophages, a bacterial cell), and, arrogating the replicative mechanism of the cell to its own purpose, multiplies within the cell, ultimately causing the cell to burst or undergo "lysis." Upon lysis, myriad new bacteriophages are released to infect other bacteria, continuing the process of proliferation. The extent of cell lysis can be visually estimated by counting plaques which are seen in a culture of host bacteria to result from localized proliferation of the bacteriophage. The number of plaques can be related to the concentration of viable phage initially present in the culture medium. At the outset, this led workers to employ plaque counting to quantitate antibody to virous bacteriophages, since the level of phage antibody present could be inversely related to the number of plaques formed by phage which survived inactivation by the antibody. The contribution of Haimovich and Sela, and of Makela, was to recognize that bacteriophage assay could be generalized by attaching immunospecific moieties to the phage, which upon immunological recognition by antibodies specific to those moieties result in phage inactivation. Accordingly, antigen under assay could be made to compete with antigen conjugated to phage for limited binding sites on antibody, and the assay target quantitated by the plaque counting method. In practice, the "chemically modified bacteriophage assay" has proven to be of general application. Thus, bacteriophage assay with a plaque counting endpoint has been employed to assay hormones such as angiotensin and insulin, proteins such as IgG, nucleic acids such as transfer RMA and DMA, enzymes such as ribonuclease and lysozyme, as well as a diverse family of haptens, such as acetyl salicylyl, penicilloyl, prostaglandins, and various nucleosides and nucleotides. In the main, such work has focused on immunological binding, but it is apparent that the bacteriophage assay may employ specific binding proteins other than antibodies, viz., circulating binding proteins and tissue macromolecules which act as receptor proteins. The bacteriophage assay described thus far provides significant advantages not common to the radioimmunoassay technique now in widespread use. The former assay does not require sophisticated counting equipment, no health hazard arises from the use of radioactive materials, unbound substrates need not be separated from bound substrates prior to quantitation, and the participants in the binding reactions enjoy substantially greater shelf lives than do the isotopes employed in radioimmunoassay. Despite the advantage conferred by bacteriophage assay in these regards, and in spite of the fact that bacteriophage assay is generally as sensitive as radioimmunoassay, the latter technique has remained the procedure of choice, it is believed, because of the strictures imposed by the plaque counting method heretofore universally employed with bacteriophage assay. Thus, while bacteriophage assay enjoys the same sensitivity and specificity which has elevated radioimmunoassay above other less cumbersome methods, that endpoint has proven a barrier to its widespread use in the diagnostic arts. This invention addresses that difficulty and, it is believed, solves it.

According to the practice of this invention, the bacteriophage assay is practiced as before through cell lysis. At that point, the assay of the invention diverges from past practice insofar as its endpoint is concerned. Thus, rather than count photolucencies in cell cultures, by my invention the assay target is quantitated by determined intracellular constituents, e.g., enzymes, emitted upon phage induced lysis. The value so determined is compared to one or more like values similarly obtained upon bacteriophage assay of standard containing known quantities of the substance under assay. The determination of one or another intracellular constituent admit of analytic techniques at least as sensitive as plaque count. But the manifold advantages of this invention derive from the greater ease and speed with which those techniques can be implemented. These and other advantages of the invention and the manner in which they are obtained will be clear from the detailed description which follows.

DETAILED DESCRIPTION OF THE INVENTION

All bacteriophage-related assays make use of the multiplication factor inherent in the phage replication process. In the case of plaque counting, upwards of 50 successive generations of phages yield a discernible plaque. In ordinary course, each plaque, though the result of lysis of numerous cells, can be taken as the artifact of a single phage present at the outset of the lytic process. Measurement of intracellular constituents by this invention is similarly advantaged by the multiplication factor conferred by phage assay, but in this case as little as a single replication or generation of phage can yield a meaningful result. That is so because the analytic techniques made available by this invention, e.g., ultraviolet spectrophotometry, colorimetry and fluorimetry, can discern the byproducts of lysis far more quickly than the eye can discern plaques which ultimately form in cell culture media. Thus, the plaque counting technique ordinarily required overnight incubation of phage and its bacterial host. Contrariwise, colorimetric or related measurement of the intracellular constituents spewed out by phage lysis can yield meaningful data within minutes of phage infection.

For essentially every intracellular constituent there exists a wavelength of maximum absorption, so that one may resort to spectrophotometry or related methodologies to quantitate a given constituent. For example, in spectrophotometry (whether ultraviolet or colorimetric), one imposes on a cuvette containing the material under assay a wavelength known to be specifically absorbed by the component to be determined. By a subtractive process, the absorption of that wavelength is related to the quantity of the component present. In related fashion, fluorimetry takes advantage of the ability of certain substances to absorb a given wavelength of incident radiation, while emitting a different wavelength, ordinarily longer. The intensity of the emitted wavelength is directly proportional to the sample content of the fluorescing substance. For convenience, hereafter all such determinations are referred to as "spectrophotometric", whether absorption spectrophotometry (as in the case of ultraviolet and colorimetric determinations) or emission spectrophotometry (as in the case of fluorometryl).

By reason of the general applicability of spectrophotometry, essentially any intracellular constituent of a lysed bacterium can be measured quantitatively by these methods. Among candidates for such determination may be mentioned, e.g., intracellular enzymes, coenzymes such nicotinamide adenine dinucleotide (NAD) and its hydrogenate (NADH), thiamine pyrophosphate ($B_1$) and flavin mononucleotide (FMN), nucleic acids such as DNA and RNA, and other substances such as adenosine triphosphate (ATP). As is well-known, all such materials admit of spectrophotometric determination of one sort or another and, indeed, various of them can be measured either by absorption or by emission spectrophotometry. For example, ATP can be fluorimetrically determined by its mediation of the luciferin-firefly luciferase reaction, whose product luciferyl adenylate fluoresces upon oxidation. Alternatively, ATP can be determined by ultraviolet spectroscopy at, e.g., 340 nanometers of the NADH end product of the successive reaction of ATP with glucose and resulting glucose-6-phosphate with NAD. Again, intracellular DNA can be monitored by ultraviolet spectroscopy, as by determining the ratio of ultraviolet absorption at 260 and 280 nanometers. From the foregoing it will be apparent that the invention finds application in the use of analytic techniques which rely upon other than the visible spectrum. However, for a number of reasons, especial advantage attends the use of colorimetric techniques to monitor intracellular constituents exposed to analysis by cell lysis. To begin with, colorimetry is cheap. It permits the use of relatively inexpensive and unsophisticated instrumentation. Secondly, interference or background absorption can be greatly reduced by the use of water-clear media as the extracellular environment in which the host bacteria are disposed for infection. Thus, while unlysed bacteria, the phage itself, etc. may be expected to absorb in the ultraviolet region, complicating ultraviolet spectroscopy, neither phage, ulysed cells nor any other extracellular substance can be expected to significantly absorb the characteristic wavelength of visible light employed to detect the intracellular constituent whose absorbence is under measurement.

In preferred embodiments of the invention, the spectrophotometric determination is advantaged by yet another multiplication factor, viz., that arising from determination of endogenous or intracellular enzyme rather than some other intracellular constituent. Enzymes are extraordinarily efficient catalysts capable of acting on their respective substrates in great numbers by reason of the very rapid turnover associated with enzymatic reactions. Thus, where the extent of cell lysis is to be determined by measurement of intracellular enzyme, a great excess of the enzyme's substrate may be added to the sample under test and the discoverable endpoint magnified all out of proportion to the quantity of enzyme originally present. At the same time, rapid turnover of substrate by the enzyme quickly yields quantifiable results.

It should be recognized that in many cases the natural substrate of given enzymes does not, when modified by the enzyme, necessarily yield a product which is readily determined by colorimetric technique. For example, the ordinary or natural substrate for beta galactosidase is lactose, and the cleavage product resulting from the lactose-beta galactosidase interaction cannot facilely be determined either colorimetrically or by ultraviolet spectrophotometry. However, the enzyme can act on a synthetic substrate such as ortho-nitrophenyl-beta-galactoside (ONBG), yielding ortho-nitrophenol. The latter compound, unlike its parent, is yellow in color and absorbs strongly in the visible region of the spectrum. Other synthetic or unnatural substrates for beta galactosidase can be posited whose enzymatic reaction products are strong and specific absorbers or emitters. In like manner, other intracellular enzymes can be colorimetrically determined by the products of their actions on different substrates. As one of many examples may be mentioned alkaline phosphatase which in nature removes the terminal phosphate from both ribo- and deoxyribooligonucleotides. Intracellular alkaline phosphatase released by lysis can be conveniently determined by providing the synthetic substrate para-nitrophenyl phosphate. Resulting para-nitrophenol can be colorimetrically determined just as in the case of ortho-nitrophenol previously discussed for the beta galactosidase case. Again, asparaginase acting on L-Asparagine and glutaminase acting on glutamine produce ammonia, colorimetrically determinable by application of the biuret method. In the light of the foregoing, diverse other enzymatic assay targets will present themselves to those ordinarily skilled in this art.

It will be appreciated that the choice of a bacterial cell will, for optimal practice of this invention, be influenced by two principal considerations, viz., its content of a readily determinable substance and the availability of a phage to infect and lyse the cell. Essentially every bacterial cell contains one or more materials amenable to colorimetric determination, and all such cells contain DNA, RNA, ATP, etc. Accordingly, optimization of the practice of the invention can proceed along lines of optimizing the bacterial content of the material determined, and this is especially so where enzyme is to be determined. Plainly, the more enzyme initially present in the bacteria, the greater will be the magnification factor from which the invention derives advantage. It is possible to induce in any given cell levels of a particular enzyme far in excess of that ordinarily present, as by culturing the bacteria in the presence of an excess of natural or synthetic substrate for the enzyme. For example, the beta galactosidase content of $E.$ $coli$ can be increased ten thousand-fold by culturing the bacteria with lactose as the only carbon source. Essentially every variety of bacteria contains inducible enzyme. Moreover, there exist bacterial strains which are "constitutive" for given enzymes. These are mutant strains which can contain as a matter of course thousands of times the enzyme present in the corresponding wild-type organism. Production of these mutant strains is especially convenient where it is desired that the mutant is constitutive for a colorimetrically determinable enzyme. Conventionally in bacteriology, those strains are prepared by ultraviolet radiation of the native bacteria, whereafter mutant strains are found out by applying to the medium in which the irradiated cells are growing the substrate for the colorimetric, enzyme-mediated reaction. The constitutive mutants are located by the resulting, strong coloration of the mutant colonies. The cell most preferred in the practice of this invention is $E.$ $coli$ which is constitutive for beta galactosidase, and that strain is available through the American Type Culture Collection 23723 Genotype: K12 lac$^+$ (i$^-$z$^+$y$^+$) thi$^-$. As another $E.$ $coli$ which is constitutive for beta galactosidase may be mentioned American Type Culture Collection 15224 ML 308.

For convenience in handling, it is preferred that the bacterial host be ordinarily nonpathogenic to man, and the $E.$ $coli$ family is one such. $B.$ $subtilis$ is another, and nonpathogenic mutants may be selected from families ordinarily considered pathogenic, e.g., Salmonella and $Staphylococcus$ $aureus.$ Additional considerations involved in the choice of bacteria are, of course, phage infectivity discussed infra, growth rate, diet, amenability to lyophilization, etc. As to the latter characteristics, for convenience and economy it is preferred that the bacteria not require exotic foodstuffs, that it undergo rapid growth, and that it can be stored for long periods in the dried state.

It is reasonable to suppose that bacteriophages exist for essentially every bacterial cell. Bacteriophages have been widely studied in the last several decades, and numerous bacteriophages, together with their host bacteria, are listed in $The$ $American$ $Type$ $Culture$ $Collection$ $Catalog$ $of$ $Strains$ (Eleventh Edition, 1974) pp. 144–149, incorporated herein by this reference. Most widely studied have been the so-called "T" phages, particularly the "T-even" phages, and phage Phi X174, each of which infect $E.$ $coli.$ The phage used in the assay of this invention, just as the phage heretofore employed in plaque counting techniques, must be conjugated to a substrate for a specific binding protein for whose binding sites the native substrate under assay competes. A wide variety of conjugation techniques have been employed and may be employed in preparing phage conjugates suitable for the practice of this invention. Thus, bifunctional reagents are commonly employed, ordinarily those reactive with amine groups presented by the proteinaceous exterior of the phage. In this category may be mentioned, e.g. glutaraldehyde, tolylene-2, 4-diisocyanate, bisdiazobenzidine and 1, 3-difluoro-2, 4-dinitrobenzene, of which the former is preferred in the present case. Other conjugation agents include water-soluble carbodiimide derivatives, which again operate principally on amine functionalities. The periodate method may be employed with selected substrates containing adjacent hydroxyl groups, e.g. nucleosides, digoxin, etc. The bond between adjacent carbons carrying the hydroxyls is opened by periodate forming aldehydes which react with amino groups of the phage, whereafter the bond is stabilized by reaction with, e.g., sodium borohydride.

As previously noted, phage assay can be employed to detect haptens, i.e., materials insufficient in size to be recognized by the immune system unless coupled to immunogens. The phage itself is immunogenic, so that in particular cases it will suffice to couple hapten directly to phage. However, accessibility of the antibody binding site to the hapten may be enhanced by first coupling hapten to a non-phage immunogen such as, e.g., keyhole limpet hemocyanin, bovine serum albumin, or the like, and then coupling the latter to the phage by conventional expedients. Again, the hapten or other substrate can be coupled to Fab', a monovalent fragment of anti-phage antibody created by papain digestion of the same. The Fab' phage binding site is then employed to affix the hapten-supplied Fab' to the phage.

Invariably, the process of conjugation will result in some degree of phage inactivation attributable to interference with the bacteria attachment mechanism of the phage. For example, glutaraldehyde employed to conjugate T-even phages may to some extent cross-link adjoining tail fibers of the phage or, indeed, bridge one phage to another, thus inactivating the phage. In each case, as is well-known, conjugation reaction conditions are tailored to ensure the survival of viable phage sufficient to the needs of subsequent steps. As will next be discussed, those steps ultimately include purposeful inactivation of phage by binding proteins specific to the substrate under assay, to the extent that inactivation is not inhibited by the native substrate in the sample under assay.

While the assay of this invention, like bacteriophage assays with plaque counting endpoints, is applicable to the detection of substrates for receptor proteins (e.g., estradiol receptor) native circulating binding proteins (e.g., thyroid binding globulin) and other non-immune binding proteins, the present invention finds its preferred application in immuno-logic assays, and for convenience the practice of the invention is hereafter described with reference to the detection of immuno-specific substances, i.e., chemical substances innately or adventitiously present in the body which are immuno-logically determinable by antibody raised to the substance itself or, in the case of a hapten, to an immuno-genic hapten-carrier conjugate. Among immunospecific substances of interest may be mentioned protein, steroid and polypeptide hormones, poisons, drugs (including drugs of abuse), hematologic factors, prostaglandins, vitamins and various enzymes. Among immunospecific substances of current commercial interest can be mentioned ACTH, aldosterone, calcitonin, carcinoma embryonic antigen, cortisol, estradiol and estriol, FSH, HGH, insulin, angiotensin, progesterone, prolactin, parathyroid hormone, T3 and T4, TBG, testosterone, TSH and nerve growth factor.

In the assay, native antigen or, as the case may be, hapten competes with the phage bound antigen (or hapten) for a limited number of binding sites on antibody supplied to the test medium. The amount of antibody available for binding to phage-conjugated antigen is inversely related to the sample content of free antigen engaged in the competition. Ideally, all phage conjugate to which antibody affixes is inactivated, i.e., rendered incapable of infecting and lysing its bacterial host. It will be appreciated that in the case of particular antigens antibody affixation to phage-bound antigen may not per se be the occasion of inactivation. In these cases, the exposure of the phage reagent to a sample under assay for the antigen may be followed by a step in which antibody to that antigen's antibody is added, i.e., so-called "complex inactivation." The anti-antibody affixes to antibody which has complexed with phage-bound antigen, ensuring inactivation of those phages which have been recognized by the antibody to antigen under test, probably by increasing the steric hindrance to bacteria attachment believed to underlie all bacteriophage assay techniques. Alternatively, antibody to the antigen under test can be cross-linked, as with glutaraldehyde, to a point short of insolublization while leaving the antibody binding sites unaffected. This greatly increases the ability of antibody to sterically hinder phage-bound antigen to which it binds.

The manner in which participants in the inactivation inhibition assay may be optimized will appear from the following example of a preferred embodiment in which the intracellular constituent determined is an enzyme, so that the additional multiplication factor associated with enzyme-substrate turnover is present. Assuming a matter of hours as a convenient completion time for the assay, one requires the lytic release of sufficient enzyme to provide, in an excess of substrate, a rapid color reaction. That quantity depends upon the level of the enzyme present in the bacteria employed and, in turn, upon the number of bacteria lysed. In the preferred case in which beta galactosidase is freed by bacteriolysis of $E.\ coli$, it is convenient to employ on the order of $10^7$ bacteria per milliliter, most preferably $4.4 \times 10^7$, and at least one order of magnitude fewer phage per milliliter, preferably at least several orders of magnitude fewer phage per milliliter, e.g., $1.5 \times 10^5$ phage per milliliter. Use of fewer phage than bacteria has a two-fold object. To begin with, phage conjugate is expensive. Secondly, if cell lysis is to be related to the extent to which phage has been inactivated, it is important to ensure that multiple hits of phage on a single bacterium do not occur to any statistically significant extent.

The following protocol may be employed in assay of nerve growth factor, an antigen associated with proliferative diseases. Nerve growth factor is conjugated with T4 phage conventionally obtained. Fifty microliters of phage ($10^{13}$ phage per milliliter) in 0.1 M phosphate buffer, pH 7 and 10 microliters of nerve growth factor (10 milligrams nerve growth factor per milliliter) are conjugated by the addition of 25 microliters of 0.05% redistilled glutaraldehyde in water, the reaction proceeding over one-half hour at room temperature. The glutaraldehyde reaction is then stopped by the addition of one additional milliliter of buffer and unbound NGF separated from phage-conjugated NGF by three successive centrifugations, each followed by the discard of supernatant and resuspension of phage in buffer.

Nerve growth factor in standards or, as the case may be, in samples of serum under test, may next be made to compete with the phage bound antigen for antibody binding sites. Thus, 100 microliters of rabbit antiserum to nerve growth factor (1:1,000 dilution), 100 microliters of phage conjugate solution ($4 \times 10^5$ phage conjugate per milliliter) and 100 microliters of test sample are combined and incubated at 37° C for 1 hour. One hundred microliters of goat antiserum to rabbit immunoglobulin (1:10 dilution) is next added to ensure inactivation of phage conjugate to which rabbit antibody has bound, and the mixture incubated for a further hour at 37° C. Next, 50 microliters of $E.\ coli$ constitutive for beta galactosidase ($4.4 \times 10^8$ bacteria per milliliter) is added and infection permitted to go forward over 1 hour at 37° C. Ortho-nitrophenyl galactoside is next added (100 microliters, 3.9 milligrams per milliliter) and incubated for one-half hour at 37° C. At this time sodium carbonate is added, both to halt the enzyme-substrate reaction and to heighten the intensity of the colored product ortho-nitrophenol. The color intensity is then conventionally read, as in a desk-top colorimeter. If known concentrations of NGF were present in the sample, the resulting value may be used in formulating a dose response curve. Contrariwise, if an unknown was under test, the resulting value can be related to NGF concentration by reference to a previously constructed dose response curve or simply read as a yes-no result by reference to some previously determined base line.

It will be appreciated that the assay described in the foregoing specification may be performed in any biological fluid, e.g., serum, plasma, urine, tears, mucosal secretions, etc., all depending upon the typical environs of the substance for which the assay is conducted.

I claim:

1. In a non-isotopic assay for a substrate for specific binding protein involving:
   (a) bacteriophage-substrate conjugate, which substrate is specifically bound by said protein; and
   (b) said protein in an amount insufficient to bind all of said conjugate;
   wherein free substrate and said conjugate compete for binding sites on the protein, protein-bound conjugate is inactivated, bacteriophage remaining viable are incubated with their host bacteria to occasion lysis and the level of said substrate in the specimen under assay is determined as an inverse function of a value corresponding to the extent of cell lysis, the improvement wherein an intracellular constituent freed by lysis is assayed, yielding a value proportional to the amount of said constituent, and the latter value is compared to one or more like values similarly obtained upon bacteriophage assay of standards containing known quantities of said substrate.

2. In a non-isotopic assay for an immunospecific substance involving:
   (a) a bacteriophage conjugate which is specifically bound by antibody to said substance; and
   (b) said antibody in an amount insufficient to bind all of said conjugate;
   wherein said substance and conjugate compete for binding sites on said antibody, antibody-bound conjugate is inactivated, bacteriophage remaining viable are incubated with their host bacteria to occasion lysis, and the level of said substance in the specimen under assay is determined as an inverse function of a value corresponding to the extent of cell lysis, the improvement wherein an intracellular constituent freed by lysis is assayed, yielding a value proportional to the amount of said constituent, and the latter value is compared to one or more like values similarly obtained upon bacteriophage assay of standards containing known quantities of said substance.

3. The method of claim 2 wherein an excess of host bacteria is employed relative to the concentration of said viable bacteriophage.

4. The method of claim 2 wherein at least one order of magnitude fewer bacteriophage than host bacteria are employed.

5. The assay of claim 4 wherein said intracellular constituent is selected from the group consisting of endogenous enzyme, nucleic acids and adenosine triphosphate.

6. The assay of claim 4 wherein said intracellular constituent is an enzyme and wherein said enzyme is present in the host bacteria in constitutive levels.

7. The assay of claim 6 wherein said bacteria is constitutive for said enzyme.

8. The assay of claim 4 wherein said intracellular constituent is an enzyme for which the host bacteria is constitutive, and wherein said enzyme is colorimetrically determined.

9. The assay of claim 8 wherein following incubation of antibody, conjugate and the sample under test, antiserum to said antibody is added.

10. The assay of claim 8 wherein said enzyme is beta galactosidase.

11. The assay of claim 8 wherein said bacteria is *E. coli* and the phage is a T-even phage.

12. The assay of claim 11 wherein said enzyme is beta galactosidase and is determined by colorimetry for orthonitrophenol.

13. In a non-isotopic assay for an immunospecific substance involving:
 (a) a bacteriophage conjugate which is specifically bound by antibody to said substance; and
 (b) said antibody in an amount insufficient to bind all of said conjugate,
 wherein said substance and conjugate compete for binding sites on said antibody, antibody-bound conjugate is inactivated, bacteriophage remaining viable are incubated with an excess of their host bacteria relative to the concentration of viable bacteriophage, and the level of said substance in the specimen under assay is determined as an inverse function of a value corresponding to the extent of cell lysis, the improvement wherein the nucleic acids freed by lysis are directly assayed by ultraviolet spectroscopy yielding a value proportional to the amount of said nucleic acid, and the latter value is compared to one or more like values similarly obtained upon bacteriophage assay of standards containing known quantities of said substance.

14. The method of claim 13 wherein at least one order of magnitude fewer bacteriophage than host bacteria are employed.

15. In a non-isotopic assay for an immuno-specific substance involving:
 (a) a bacteriophage conjugate which is specifically bound by antibody to said substance; and
 (b) said antibody in an amount insufficient to bind all of said conjugate,
 wherein said substance and conjugate compete for binding sites on said antibody, antibody-bound conjugate is inactivated, bacteriophage remaining viable are incubated with an excess of their host bacteria relative to the concentration of viable bacteriophage, and the level of said substance in the specimen under assay is determined as an inverse function of a value corresponding to the extent of cell lysis, the improvement wherein adenosine triphosphate freed by lysis is indirectly assayed by fluorimetric determination of the oxidation product of luciferyl adenylate produced by the operation of firefly luciferase upon its substrate luciferin as mediated by the intracellular adenosine triphosphate released by cell lysis, thereby yielding a value proportional to the amount of the adenosine triphosphate, and the latter value is compared to one or more like values similarly obtained upon bacteriophage assay of standards containing known quantities of said substance.

16. The method of claim 15 wherein at least one order of magnitude fewer bacteriophage than host bacteria are employed.

* * * * *